US010654854B2

(12) United States Patent
Li et al.

(10) Patent No.: US 10,654,854 B2
(45) Date of Patent: May 19, 2020

(54) SALTS AND CRYSTALS OF ITI-007

(71) Applicant: INTRA-CELLULAR THERAPIES, INC., New York, NY (US)

(72) Inventors: Peng Li, New Milford, NJ (US); Edwin Aret, Almere (NL)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 16/090,144

(22) PCT Filed: Mar. 28, 2017

(86) PCT No.: PCT/US2017/024562
§ 371 (c)(1),
(2) Date: Sep. 28, 2018

(87) PCT Pub. No.: WO2017/172784
PCT Pub. Date: Oct. 5, 2017

(65) Prior Publication Data
US 2019/0112309 A1 Apr. 18, 2019

Related U.S. Application Data (60) Provisional application No. 62/314,326, filed on Mar. 28, 2016.

(51) Int. Cl.
C07D 471/16 (2006.01)
A61P 25/18 (2006.01)

(52) U.S. Cl.
CPC ............ C07D 471/16 (2013.01); A61P 25/18 (2018.01); *C07B 2200/13* (2013.01)

(58) Field of Classification Search
CPC .................................................... C07D 471/16
USPC .......................................................... 546/64
See application file for complete search history.

(56) References Cited

U.S. PATENT DOCUMENTS

| | | | |
|---|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 4,522,944 A | 6/1985 | Doria et al. |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,576,460 A | 11/1996 | Buchwald et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,847,166 A | 12/1998 | Buchwald et al. |
| 5,902,901 A | 5/1999 | Goodbrand et al. |
| 6,043,370 A | 3/2000 | Kubo et al. |
| 6,166,226 A | 12/2000 | Buchwald et al. |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,465,693 B2 | 10/2002 | Buchwald et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |

(Continued)

FOREIGN PATENT DOCUMENTS

| | | |
|---|---|---|
| EP | 0856508 | 8/1998 |
| EP | 1245553 | 10/2002 |

(Continued)

OTHER PUBLICATIONS

Vippagunta; Advanced Drug Delivery Reviews 2001, 48, 3-26. (Year: 2001).*
Rubi; Endocrinology 2010, 151, 5570-5581. (Year: 2010).*
Alvir, J., et al., "Clozapine-Induced Agranulocytosis. Incidence and Risk Factors in the United States," The New England Journal of Medicine, 329(3): 162-167 (1993).
Angst, J., et al., "Prevalence and Characteristics of Undiagnosed Bipolar Disorders in Patients With a Major Depressive Episode," Arch. Gen. Psychiatry, 68(8): 701-709 (2011).
Avendaño, C., et al., "The Problem of the Existence of C(Ar)—H . . . N Intramolecular Hydrogen Bonds in a Family of 9-Azaphenyl-9H-carbazoles," J. Chem. Soc. Perkin. Trans., 2: 1547-1555 (1993).
Balbach, S., et al., "Pharmaceutical evaluation of early development candidates 'the 100 mg-approach,'" International Journal of Pharmaceutics, 275: 1-12 (2004).

(Continued)

*Primary Examiner* — Daniel R Carcanague
(74) *Attorney, Agent, or Firm* — Hoxie & Associates LLC (57) ABSTRACT

The disclosure provides new, stable, pharmaceutically acceptable salt forms of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one, together with methods of making and using them, and pharmaceutical compositions comprising them.

18 Claims, 3 Drawing Sheets

(56) References Cited

U.S. PATENT DOCUMENTS

| | | |
|---|---|---|
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,592,454 B2 | 9/2009 | Lee et al. |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,616,061 B2 | 4/2017 | Mates et al. |
| 9,708,322 B2 | 7/2017 | Li et al. |
| 9,751,883 B2 | 9/2017 | Tomesch et al. |
| 9,956,227 B2 | 5/2018 | Vanover et al. |
| 2001/0008942 A1 | 7/2001 | Buchwald et al. |
| 2004/0034015 A1 | 2/2004 | Robichaud et al. |
| 2005/0127482 A1 | 6/2005 | Fauty et al. |
| 2005/0222209 A1 | 10/2005 | Zeldis et al. |
| 2006/0205787 A1 | 9/2006 | Muller et al. |
| 2015/0072964 A1 | 3/2015 | Mates et al. |
| 2015/0080404 A1 | 3/2015 | Mates et al. |
| 2019/0112310 A1* | 4/2019 | Li .................. C07D 471/16 |

FOREIGN PATENT DOCUMENTS

| | | |
|---|---|---|
| EP | 1254884 | 11/2002 |
| EP | 1564671 | 8/2005 |
| WO | WO 1998/015515 | 4/1998 |
| WO | WO 1999/043643 | 9/1999 |
| WO | WO 2000/002887 | 1/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/085838 | 10/2002 |
| WO | WO 2004/013094 | 2/2004 |
| WO | WO 2004/039788 | 5/2004 |
| WO | WO 2004/056324 | 7/2004 |
| WO | WO 2006/081251 | 8/2006 |
| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/114181 | 9/2009 |
| WO | WO 2009/145900 | 12/2009 |
| WO | WO 2013/155504 | 10/2013 |
| WO | WO 2013/155506 | 10/2013 |
| WO | WO 2014/145192 | 9/2014 |
| WO | WO 2015/085004 | 6/2015 |

OTHER PUBLICATIONS

Bastin, R.J., et al., "Salt Selection and Optimisation Procedures for Pharmaceutical New Chemical Entities," Organic Process Research & Development, 4(5): 427-435 (2000).

Beletskaya, I., et al., "Pd- and Cu-catalyzed selective Arylation of Benzotriazole," Tetrahedron Letters, 39: 5617-5620 (1998).

Berger, J., et al., "Synthesis of Some Conformationally Restricted Analogues of Fentanyl," Journal of Medicinal Chemistry, 20(4): 600-602 (1977).

Boger, D., et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5, 8-quinone Ring System," J. Org. Chem., 50: 5782-5789 (1985).

Bowman, W.R., et al., "Copper(1) Catalysed Aromatic Nucleophilic Substitution: A Mechanistic and Synthetic Comparison with the SRN1 Reaction," Tetrahedron Letters, 25(50): 5821-5824 (1984).

Bowman, W.R., et al., "Intramolecular Aromatic Substitution (SRN1) Reactions, Use of Entrainment for the Preparation of Benzothiazoles," Tetrahedron Letters, 23(48): 5093-5096 (1982).

Bowman, W.R., et al., "Synthesis of 1H-quinazoline-4-ones using intramolecular aromatic nucleophilic substitution," ARKIVOC, x: 434-442 (2003).

Byrn, S., et al., "Pharmaceutical Solids: A Strategic Approach to Regulatory Considerations," Pharmaceutical Research, 12(7): 945-954 (1995).

Crawford, K., et al., "Copper-catalyzed amidations of bromo substituted furans and thiophenes," Tetrahedron Letters, 43: 7365-7368 (2002).

Davis, R., et al., "ITI-007 demonstrates brain occupancy at sertonin 5-HT2A and dopamine D2 receptors and serotonin transporters using positron emission tomography in healthy volunteers," Psychopharmacology, Published Online Apr. 7, 2015, pp. 1-10.

Davis, R., et al., "ITI-007 in the treatment of schizophrenia: from novel pharmacology to clinical outcomes," Expert Review of Neurotherapeutics, 16(6): 601-614 (2016).

Evindar, G., et al., "Copper- and Palladium-Catalyzed Intramolecular Aryl Guanidinylation: An Efficient Method for the Synthesis of 2-Aminobenzimidazoles," Organic Letters, 5(2): 133-136 (2003).

Ezquerra, J., et al., "Efficient Reagents for the Synthesis of 5-, 7-, and 5,7-Substituted Indoles Starting from Aromatic Amines: Scope and Limitations," J. Org. Chem., 61: 5804-5812 (1996).

Fee, W.W., et al., "Copper (II)—Promoted Solvolyses of Nickel(II) Complexes III. Tetradentate Schiff Base Ligands Containing Various Diamine Segments," Aust. J. Chem., 26: 1475-1485 (1973).

Ferreira, I., et al., "Novel synthetic routes to thienocarbazoles via palladium or copper catalyzed amination or amidation of arylhalides and intramolecular cyclizaiton," Tetrahedron, 58: 7943-7949 (2002).

Finet, J., et al., "Recent Advances in Ullmann Reaction: Copper(II) Diacetate Catalysed N-, O- and S-Arylation Involving Polycoordinate Heteroatomic Derivatives," Current Organic Chemistry, 6: 597-626 (2002).

Fitzgerald, R., et al., "Inhibition of Caries in Hamsters by 2-Deoxy-D-Glucose," J. Dent. Res., 56(11): 1431 (1977).

Goodbrand, H.B., et al., "Ligand-Accelerated Catalysis of the Ullmann Condensation: Application to Hole Conducting Triarylamines," J. Org. Chem., 64: 670-674 (1999).

Grant, "Polymorphism in Pharmaceutical Solids," Chapter 1, 1-10 (1999).

Guillory, "Polymorphism in Pharmaceutical Solids," Chapter 5, 183-226 (1999).

Hackam, D., et al., "Translation of Research Evidence From Animals to Humans," JAMA, 296(14): 1731-1732 (2006).

Hamann, B., et al., "Systematic Variation of Bidentate Ligands Used in Aryl Halide Amination. Unexpected Effects of Steric, Electronic, and Geometric Perturbations," J. Am. Chem. Soc., 120: 3694-3707 (1998).

Hartwig, J.F., "Palladium-Catalyzed Amination of Aryl Halides: Mechanism and Rational Catalyst Design," Synlett, 329-340 (1996).

Hassan, J., et al., "Aryl-aryl bond formation one century after the discovery of the ullmann reaction," Chem. Rev., 102: 1359-1469 (2002).

Haynes, D., et al., "Occurrence of Pharmaceutically Acceptable Anions and Cations in the Cambridge Structural Database," Journal of Pharmaceutical Sciences, 94(10): 2111-2120 (2005).

International Search Report for International Application No. PCT/US2009/003261, dated Jul. 16, 2009, 3 pages.

International Search Report for International Application No. PCT/US2017/024562, dated Jun. 27, 2017, 2 pages.

International Search Report for International Application No. PCT/US2017/024597, dated Jun. 27, 2017, 3 pages.

Ito, T., et al., "Studies of Organic Catalytic Reactions. VI. The Function of Pyridine and Copper in the Rosenmund-von Braun reaction," Bulletin of the Chemical Society of Japan, 41: 419-423 (1968).

Jain, N.K., et al., "Polymorphism in Pharmacy," Indian Drugs, 23(6): 315-316 (1986).

(56) References Cited

OTHER PUBLICATIONS

Ji, J., "Selective Amination of Polyhalpyridines Catalyzed by a Palladium-Xantphos Complex," Organic Letters, 5(24): 4611-4614 (2003).
Jordan, V.C., "Tamoxifen: A Most Unlikely Pioneering Medicine," Nature Reviews: Drug Discovery, 2: 205-213 (2003).
Kametani, T., et al., "A Novel Synthesis of Indole Derivatives," Heterocycles, 14(3): 277-280 (1980).
Kang, S.K., "Copper-catalyzed N-Arylation of Aryl Iodides with Benzamides or Nitrogen Heterocycles in the Presence of Ethylenediamine," Synlett, 3: 427-430 (2002).
Kiyomori, A., et al., "An Efficient Copper-Catalyzed Coupling of Aryl Halides with Imidazoles," Tetrahedron Letters, 40: 2657-2660 (1999).
Klapars, A., et al., "A General and Efficient Copper Catalyst for the Amidation of Aryl Halides," J. Am. Chem. Soc., 124: 7421-7428 (2002).
Klapars, A., et al., "A General and Efficient Copper Catalyst for the Amidation of Aryl Halides and the N-Arylation of Nitrogen Heterocycles," J. Am. Chem. Soc., 123: 7727-7729 (2001).
Kondratov, S.A., et al., "Nucleophilic Substitution in the Aromatic Series. LV. Reaction of o-Nitrochlorobenzene with Ammonia in the Presence of Copper Compounds," Zhurnal Organidreskoi Khimii, 51(11): 2387-2390 (1979).
Kwong, F., et al., "Mild and Efficient Copper-Catalyzed Amination of Aryl Bromides with Primary Alkylamines," Organic Letters, 5(6): 793-796 (2003).
Lee, T., et al., "Novel, Highly Potent, Selective 5-HT2A/D2 Receptor Antagonists as Potential Atypical Antipsychotics," Bioorganic & Medicinal Chemistry Letters, 13: 767-770 (2003).
Li, J., et al., "New polymorphs of isonicotinamide and nicotinamide," Chem. Commun., 47: 1530-1532 (2011).
Li, P., et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, 57: 2670-2682 (2014).
Louie, J., et al., "Palladium-Catalyzed Synthesis of Arylamines from Aryl Halides. Mechanistic Studies Lead to Coupling in the Absence of Tin Reagents," Tetrahedron Letters, 36(21): 3609-3612 (1995).
Marcoux, J., et al., "A General Copper-Catalyzed Synthesis of Diaryl Ethers," J. Am. Chem. Soc., 119: 10539-10540 (1997).
Marek, G., et al., "Synergistic Action of 5-HT2A Antagonists and Selective Serotonin Reuptake Inhibitors in Neuropsychiatric Disorders," Neuropsychopharmacology, 28: 402-412 (2003).
Mulrooney, C.A., "Recent Developments in Copper-Catalyzed N-Arylation with Aryl Halides," Essay—University of Pennsylvania. (2004).
Murakami, et al., Chem. Pharm. Bull., 43(8): 1281-1286 (1995).
Nagai, Y., et al., "Synthesis of 2,3,4,4a,5,9b-Hexahydro-1H-pyrido[4,3-b]indole Derivatives and Their Central Nervous System Activities," Journal of Medicinal Chemistry, 22(6): 677-683 (1979).
Newman, A., et al., "Solid-state analysis of the active pharmaceutical ingredient in drug products," Drug Discovery Today, 8(9): 898-903 (2003).
Perlis, R., et al., "Clinical Features of Bipolar Depression Versus Major Depressive Disorder in Large Multicenter Trials," Am. J. Psychiatry, 163: 225-231 (2006).
"Protection for the Amino Group," Protective Groups in Organic Synthesis, Third Edition, John Wiley & Sons, Inc., 494-505 (1999).
Rackova, L., et al., "Free Radical Scavenging and Antioxidant Activities of Substituted Hexahydropyridoindoles. Quantitative Structure—Activity Relationships," J. Med. Chem., 49: 2543-2548 (2006).
Rye, D.B., "Sleep Disorders and Parkinson's Disease," American Parkinson Disease Association, 2000, 2 pages, URL: <http://www.waparkinsons.org/edu_research/articles/Sleep_Disorders.html>.
Sadighi, J., et al., "A Highly Active Palladium Catalyst System for the Arylation of Anilines," Tetrahedron Letters, 39: 5327-5330 (1998).
Savjani, K., et al., "Drug Solubility: Importance and Enhancement Techniques," International Scholarly Research Network Pharmaceutics, 2012: 1-10 (2012).
Sigel, H., et al., "Ternary Complexes in Solution. XVI. Influence of the Size of the Chelate Rings on the Stability of Mixed-Ligand Copper(II) Complexes Containing Aliphatic Ligands," Inorganic Chemistry, 13(2): 462-465 (1974).
Singhal, D., et al., "Drug polymorphism and dosage form design: a practical perspective," Advanced Drug Delivery Reviews, 56: 335-347 (2004).
Skoog, "Principles of Instrumental Analysis, 4th Edition," 577 (1992).
Smith, A.D., et al., "Oxford Dictionary of Biochemistry and Molecular Biology," Oxford University Press, 145 (1997).
Snyder, G., et al., "Functional profile of a novel modulator of serotonin, dopamine, and glutamate neurotransmission," Psychopharmacology, 232: 605-621 (2015).
Sugahara, M., et al., "A Facile Copper-Catalyzed Ullmann Condensation: N-Arylation of Heterocyclic Compounds Containing an-NHCO-Moiety," Chem. Pharm. Bull., 45(4): 719-721 (1997).
Wagaw, S., et al., "A Palldium-Catalyzed Method for the Preparation of Indoles via the Fischer Indole Synthesis," Journal of the American Chemical Society, 121(44): 10251-10263 (1999).
Wolfe, J., et al., "An Improved Catalyst System for Aromatic Carbon-Nitrogen Bond Formation: The Possible Involvement of Bis(Phosphine) Palladium Complexes as Key Intermediates," J. Am. Chem. Soc., 118: 7215-7216 (1996).
Wolfe, J., et al., "Intramolecular Palladium-Catalyzed Aryl Amination and Aryl Amidation," Tetrahedron, 52(21): 7525-7546 (1996).
Wolter, M., et al., "Synthesis of N-Aryl Hydrazides by Copper-Catalyzed Coupling of Hydrazides with Aryl Iodides," Organic Letters, 3(23): 3803-3805 (2001).
Yamada, K., et al., "A Mild Copper-mediated Intramolecular Amination of Aryl Halides," Synlett, 2: 231-234 (2002).
Yang, B., et al., "The development of efficient protocols for the palladium-catalyzed cyclization reactions of secondary amides and carbamates," Organic Letters, 1(1): 35-37 (1999).
Zhang, Z., et al., "Highly efficient copper-catalyzed N-arylation of alkylamines with aryl iodides using phosphoramidite as ligand," Catalysis Communications, 6: 784-787 (2005).

* cited by examiner

SALTS AND CRYSTALS OF ITI-007

CROSS-REFERENCE TO RELATED APPLICATIONS

This application is a United States Application under 35 U.S.C. § 371 claiming priority to and the benefit of PCT Application No. PCT/US2017/024562, filed Mar. 28, 2017, which claims priority to and the benefit of U.S. Provisional Application Ser. No. 62/314,326, filed on Mar. 28, 2016, the contents of each of which are hereby incorporated by reference in their entireties.

FIELD

This disclosure relates to certain novel salts and crystal forms of a substituted heterocycle fused gamma-carboline, the manufacture thereof, pharmaceutical compositions thereof, and use thereof, e.g., in the treatment of diseases or abnormal conditions involving or mediated by the 5-$HT_{2A}$ receptor, serotonin transporter (SERT), and/or dopamine $D_1/D_2$ receptor signaling pathways.

BACKGROUND 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, or as ITI-007), has the following structure:

ITI-007 is a potent 5-HT2A receptor ligand (Ki=0.5 nM) with strong affinity for dopamine (DA) D2 receptors (Ki=32 nM) and the serotonin transporter (SERT) (Ki=62 nM) but negligible binding to receptors (e.g., H1 histaminergic, 5-HT2C, and muscarinic) associated with cognitive and metabolic side effects of antipsychotic drugs. ITI-007 is currently in clinical trials, i.a., for treatment of schizophrenia. While ITI-007 is a promising drug, its production and formulation present challenges. In free base form, ITI-007 is an oily, sticky solid, with poor solubility, not only in water but also in many organic solvents. Making salts of the compound has proven to be unusually difficult. A hydrochloride salt form of ITI-007 was disclosed in U.S. Pat. No. 7,183,282, but this salt is hygroscopic and shows poor stability. A toluenesulfonic acid addition salt (tosylate) of ITI-007 was finally identified and described in WO 2009/114181.

There is a need for alternative stable and pharmaceutically acceptable salts and polymorphs of ITI-007.

SUMMARY

In an effort to find new salts and polymorphs of ITI-007, an extensive salt screen was undertaken. In initial efforts, only the hydrochloride was identified, but this proved to be hygroscopic and poorly stable. The compound does not readily form salts with other common, pharmaceutically acceptable acids. Eventually, a toluenesulfonic acid addition salt (tosylate) was prepared, as described in WO 2009/114181, but no other stable salts were found. Finally, a major salt screen was carried out, wherein the free base compound was studied in different solvent systems and under different conditions, and then systematically screened using a selection of over 100 acids under different conditions and with different solvent, co-solvent and anti-solvent systems, to identify possible salt forms. Following extensive screening and experimentation, the following novel salts were discovered, characterized, and found to be reproducible and stable: oxalate, 4-aminosalicylate, and cyclamate.

The disclosure thus provides novel oxalate, 4-aminosalicylate, and cyclamate salt forms of ITI-007, and polymorphs thereof, which are especially advantageous for use in the preparation of galenic formulations, together with methods of making and using the same.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Oxalate Salts

In a first embodiment, the invention provides 1-(4-fluorophenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in oxalate salt form (Salt 1). The invention therefore provides the following:

1.1. Salt 1 in solid form.
1.2. Salt 1 or 1.1 in dry crystalline form.
1.3. Salt 1.2 in a homogeneous crystal form, free or substantially free of other forms, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous forms.

1.4. Any foregoing form of Salt 1 in crystalline form, when crystallized from a mixture of oxalic acid and ITI-007, e.g. in an organic solvent, e.g., comprising toluene, ethyl acetate or mixtures thereof; e.g., wherein the oxalic acid and ITI-007 are in a molar ratio of about 1:1, and the solvent is ethyl acetate.

1.5. Any foregoing form of Salt 1 which is a solvate, e.g., an ethyl acetate solvate.

1.6. Any foregoing form of Salt 1 which is not a solvate.

1.7. Any foregoing form of Salt 1 which is a hydrate.

1.8. Any foregoing form of Salt 1 which is not a hydrate.

1.9. Any foregoing form of Salt 1 formed by combining free ITI-007 free base and oxalic acid in a 1:1 molar ratio.

1.10. Any foregoing form of Salt 1 wherein a DSC analysis shows two endothermic events, at 83° C. and 219° C.; e.g. wherein a DSC/TGA analysis shows the first endothermic event at $T_{onset}$=74.5° C., $T_{peak}$=83.3° C. and $\Delta E$=−6.0 J/g and the second at $T_{onset}$=194.2° C., $T_{peak}$=218.6° C. and $\Delta E$=−162.1.0 J/g.

1.11. Any foregoing form of Salt 1, in the form of a crystal having an X-ray powder diffraction pattern corresponding to the d-spacing and/or angle (2-theta) values of the following table, for example at least five, or at least six, or at least seven, or at least eight of said values, e.g., taking into account potential variations due to sample purity and instrument variation, for example 2θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.4, e.g., at least 0.5, e.g., at least 0.6, e.g., comprising peaks 1, 2, 6, 7, 8, and 9:

| XRPD (Cu anode, Ni filter) for Oxalate Salt Crystal | | | |
| --- | --- | --- | --- |
| # | Angle | d Value | Rel. Intensity |
| 1 | 11.36753 | 7.77784 | 0.505801 |
| 2 | 11.4984 | 7.689606 | 0.535533 |
| 3 | 13.63323 | 6.489913 | 0.201991 |
| 4 | 14.90435 | 5.939156 | 0.242149 |
| 5 | 16.28162 | 5.439727 | 0.225224 |
| 6 | 17.06375 | 5.192113 | 1 |
| 7 | 17.08605 | 5.185387 | 0.95063 |
| 8 | 18.92882 | 4.684528 | 0.973955 |
| 9 | 18.98987 | 4.669604 | 0.896333 |
| 10 | 20.91385 | 4.244165 | 0.483429 |
| 11 | 22.84175 | 3.890119 | 0.493607 |
| 12 | 23.80149 | 3.735387 | 0.38255 |
| 13 | 24.77138 | 3.591286 | 0.36959 |

1.12. Any foregoing form of Salt 1, in the form of a crystal having an X-ray powder diffraction pattern corresponding to FIG. 1, e.g., taking into account potential variations due to sample purity and instrument variation, for example 2θ shifts due to variation in X-ray wavelength, e.g., an X-ray powder diffraction pattern corresponding to FIG. 1 generated using an X-ray diffractometer with a copper anode and a nickel filter.

1.13. Any foregoing form of Salt 1, in the form of a crystal having an X-ray powder diffraction pattern having at least 5, or at least 6, or at least 7, or at least 8, peaks having angle (2-theta) values selected from the group consisting of about 11.37, 11.50, 13.63, 14.90, 16.28, 17.06, 17.09, 18.93, 18.99, 20.91, 22.84, 23.80, and 24.77, taking into account potential variations due to sample purity and instrument variation, wherein the X-ray powder diffraction pattern is generated using an X-ray diffractometer with a copper anode and a nickel filter.

1.14. Any foregoing form of Salt 1, in the form of a crystal having an X-ray powder diffraction pattern having at least 5, or at least 6, or at least 7, or at least 8, peaks having d-spacing values selected from the group consisting of about 7.78, 7.69, 6.49, 5.93, 5.44, 5.19, 5.18, 4.68, 4.67, 4.24, 3.89, 3.74, and 3.59, taking into account potential variations due to sample purity and instrument variation, wherein the X-ray powder diffraction pattern is generated using an X-ray diffractometer with a copper anode and a nickel filter.

1.15. Any foregoing form of Salt 1, in the form of a crystal having an X-ray powder diffraction pattern having at least 5, or at least 6, or at least 7, or at least 8, peaks having angle (2-theta) values and/or d-spacing values as provided in 1.13 and 1.14.

1.16. Any foregoing form of Salt 1, in the form of a crystal having an X-ray powder diffraction powder having relative angle (2-theta) values as provided in the table of embodiment 1.11, wherein the values are shifted by up to +/−0.2 degrees, e.g., wherein the values are substantially uniformly shifted by up to +/−0.2 degrees.

1.17. Any foregoing form of Salt 1 wherein the ITI-007 is deuterated, e.g., wherein the deuterium:protium ratio at one or more specified positions in the molecule is significantly higher, e.g., at least 2×, for example at least 10× higher, than the natural isotope ratios or the isotope ratios at other positions in the molecule at; for example, any foregoing form of Salt 1 wherein the —CH2- adjacent to the methylated nitrogen moiety and/or adjacent to the carbonyl moiety of ITI-007 is deuterated, e.g., is in the form of —CHD- or —CD2- at levels which are significantly higher than the natural deuterium:protium isotope ratio or the deuterium:protium isotope ratio at other positions in the molecule, and/or wherein the methyl group is deuterated, e.g., is CD3-, e.g., at levels which are significantly higher than the natural deuterium:protium isotope ratio or the deuterium:protium isotope ratio at other positions in the molecule, e.g., as described in WO 2015/154025, the contents of which are incorporated herein by reference.

1.18. Any foregoing form of Salt 1 exhibiting any combination of characteristics as described in 1.1-1.17.

In another embodiment, the invention provides a process (Process 1) for the production of Salt 1, comprising (a) reacting 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with oxalic acid, e.g., together with an organic solvent, e.g., e.g., comprising toluene, ethyl acetate or mixtures thereof; e.g., wherein the oxalic acid and ITI-007 are in a molar ratio of about 1:1, and the solvent is ethyl acetate; and (b) recovering the oxalate salt thus formed, e.g., recovering an oxalate salt according to any of Salt 1, et seq. above.

In another embodiment, the invention provides a method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising reacting a crude solution of ITI-007 with oxalic acid, and recovering the oxalate salt thus formed, e.g., in accordance with Process 1, and optionally converting the oxalate salt back to ITI-007 free base or to another salt form.

In another embodiment, the invention provides the use of oxalic acid in a method of isolating and/or purifying ITI-007.

In another embodiment, the invention provides a pharmaceutical composition comprising Salt 1, e.g., any of Salt 1.1-1.18, as active ingredient, in combination or association with a pharmaceutically acceptable diluent or carrier.

In another embodiment, the invention provides pharmaceutical composition comprising Salt 1, e.g., any of Salt 1.1-1.18, as active ingredient, in combination or association with a pharmaceutically acceptable diluent or carrier, wherein the Salt 1 is predominantly, or is entirely or substantially entirely, in dry crystalline form.

In a particular embodiment, the invention provides a pharmaceutical composition comprising Salt 1, e.g., any of Salt 1.1-1.18, as active ingredient, in combination or association with a pharmaceutically acceptable diluent or carrier, in the form of an injectable depot form, to provide extended release of ITI-007.

In another embodiment, the invention provides Salt 1, e.g., any of Salt 1.1-1.18, or a pharmaceutical composition comprising Salt 1, e.g., any of Salt 1.1-1.18, for use in treating a disease or abnormal condition involving or mediated by the 5-$HT_{2A}$ receptor, serotonin transporter (SERT), and/or dopamine $D_1/D_2$ receptor signaling pathways, e.g., a disorder selected from obesity, anorexia, bulemia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia.

In another embodiment, the invention provides a method for the prophylaxis or treatment of a human suffering from a disease or abnormal condition involving or mediated by the 5-$HT_{2A}$ receptor, serotonin transporter (SERT), and/or dopamine $D_1/D_2$ receptor signaling pathways, e.g., a disorder selected from obesity, anorexia, bulemia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia, comprising administering to a patient in need thereof a therapeutically effective amount of any of Salt 1, et seq.

4-aminosalicylate Salts

In another embodiment, the invention provides 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in 4-aminosalicylate salt form (Salt 2). The invention therefore provides the following:

2.1. Salt 2 in solid form.
2.2. Salt 2 or 2.1 in dry crystalline form.
2.3. Salt 2.2 in a homogeneous crystal form, free or substantially free of other forms, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous forms.
2.4. Any foregoing form of Salt 2 in crystalline form, when crystallized from a mixture of 4-aminosalicylic acid e.g. in an organic solvent, e.g., comprising methanol; e.g., wherein the 4-aminosalicylic acid and ITI-007 are in a molar ratio of about 1:1, the solvent is methanol, and dibutylether is added as an anti-solvent to precipitate the crystal.
2.5. Any foregoing form of Salt 2 which is a solvate, e.g., a methanol solvate.
2.6. Any foregoing form of Salt 2 which is not a solvate.
2.7. Any foregoing form of Salt 2 which is a hydrate.
2.8. Any foregoing form of Salt 2 which is not a hydrate.
2.9. Any foregoing form of Salt 2 formed by combining free ITI-007 free base and 4-aminosalicylic acid in a 1:1 molar ratio.
2.10. Any foregoing form of Salt 2 wherein a DSC analysis shows two endothermic events, at 125° C. and 166° C.; e.g. wherein a DSC/TGA analysis shows the first endothermic event at $T_{onset}$=119.1° C., $T_{peak}$=125.4° C. and ΔE=−26.8 J/g and the second at $T_{onset}$=142.3° C., $T_{peak}$=166.3° C. and ΔE=−115.9 J/g; e.g., wherein TGA shows three different mass losses, 1.8% in the temperature range of 40° C.-120° C., 10.8% in the temperature range 120° C.-190° C. and 13.8% in the temperature range of 190-260° C.
2.11. Any foregoing form of Salt 2, in the form of a crystal having an X-ray powder diffraction pattern corresponding to the d-spacing and/or angle (2-theta) values from the following table, for example at least five, or at least six, or at least seven, or at least eight of said values, e.g., taking into account potential variations due to sample purity and instrument variation, for example 2θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.4, e.g., at least 0.5, e.g., at least 0.6, e.g., comprising peaks 5, 6, and 19:

| XRPD (Cu anode, Ni filter) for 4-Aminosalicylate Salt Crystal | | | |
|---|---|---|---|
| # | Angle | d Value | Rel. Intensity |
| 1 | 6.74126 | 13.10153 | 0.09900139 |
| 2 | 7.11907 | 12.40705 | 0.03797358 |
| 3 | 8.37464 | 10.54953 | 0.1528345 |
| 4 | 11.10135 | 7.963726 | 0.04906989 |
| 5 | 12.24933 | 7.219841 | 0.7057194 |
| 6 | 12.44248 | 7.108195 | 1 |
| 7 | 13.22133 | 6.691157 | 0.4287872 |
| 8 | 13.39928 | 6.602692 | 0.2176722 |
| 9 | 14.84852 | 5.96136 | 0.0594308 |
| 10 | 15.20714 | 5.821574 | 0.08040762 |
| 11 | 16.11707 | 5.494892 | 0.3971254 |
| 12 | 16.77107 | 5.28206 | 0.1820023 |
| 13 | 17.7106 | 5.003911 | 0.1346539 |
| 14 | 17.7024 | 5.006211 | 0.117254 |
| 15 | 18.18279 | 4.875015 | 0.2468108 |
| 16 | 18.8011 | 4.716061 | 0.3306873 |
| 17 | 18.97436 | 4.673387 | 0.3899686 |
| 18 | 19.70455 | 4.501822 | 0.3229629 |
| 19 | 20.18032 | 4.396748 | 0.6070609 |
| 20 | 20.6671 | 4.294276 | 0.2430615 |
| 21 | 21.48864 | 4.131919 | 0.3574843 |
| 22 | 22.0719 | 4.024034 | 0.307444 |
| 23 | 22.47136 | 3.953394 | 0.270866 |
| 24 | 23.8674 | 3.72522 | 0.1904099 |
| 25 | 24.28923 | 3.661472 | 0.1862242 |
| 26 | 24.39947 | 3.645177 | 0.1742721 |

-continued

XRPD (Cu anode, Ni filter) for 4-Aminosalicylate Salt Crystal

| # | Angle | d Value | Rel. Intensity |
|---|---|---|---|
| 27 | 24.93711 | 3.567793 | 0.09287543 |
| 28 | 25.24371 | 3.52515 | 0.1587876 |
| 29 | 25.98695 | 3.425991 | 0.3154892 |
| 30 | 26.41592 | 3.37132 | 0.1229696 |
| 31 | 27.28763 | 3.26557 | 0.1484904 |
| 32 | 27.30054 | 3.264055 | 0.1485404 |
| 33 | 28.05261 | 3.178234 | 0.03697395 |
| 34 | 30.12185 | 2.964448 | 0.0494277 |
| 35 | 33.52555 | 2.670852 | 0.02418169 |
| 36 | 35.96252 | 2.495255 | 0.0386623 |
| 37 | 36.2068 | 2.478979 | 0.03238863 |
| 38 | 36.07337 | 2.487841 | 0.04954784 |

2.12. Any foregoing form of Salt 2, in the form of a crystal having an X-ray powder diffraction pattern corresponding to FIG. 2, e.g., taking into account potential variations due to sample purity and instrument variation, for example 2θ shifts due to variation in X-ray wavelength, e.g., an X-ray powder diffraction pattern corresponding to FIG. 3 generated using an X-ray diffractometer with a copper anode and a nickel filter.

2.13. Any foregoing form of Salt 2, in the form of a crystal having an X-ray powder diffraction pattern having at least 5, or at least 6, or at least 7, or at least 8, peaks having angle (2-theta) values selected from the group consisting of about 6.74, 7.12, 8.37, 11.10, 12.25, 12.44, 13.22, 13.40, 14.85, 15.21, 16.12, 16.77, 17.70, 17.71, 18.19, 18.80, 18.97, 19.70, 20.18, 20.67, 21.49, 22.07, 22.47, 23.87, 24.29, 24.40, 24.94, 25.24, 25.99, 26.42, 27.29, 27.30, 28.05, 30.12, 33.53, 35.96, 36.21, and 36.07, taking into account potential variations due to sample purity and instrument variation, wherein the X-ray powder diffraction pattern is generated using an X-ray diffractometer with a copper anode and a nickel filter.

2.14. Any foregoing form of Salt 2, in the form of a crystal having an X-ray powder diffraction pattern having at least 5, or at least 6, or at least 7, or at least 8, peaks having d-spacing values selected from the group consisting of about 13.10, 12.41, 10.55, 7.96, 7.22, 7.11, 6.69, 6.60, 5.96, 5.82, 5.49, 5.28, 5.01, 5.00, 4.88, 4.72, 4.67, 4.50, 4.40, 4.29, 4.13, 4.02, 3.95, 3.73, 3.66, 3.65, 3.57, 3.53, 3.43, 3.37, 3.27, 3.26, 3.18, 2.96, 2.67, 2.50, 2.49, and 2.48, taking into account potential variations due to sample purity and instrument variation, wherein the X-ray powder diffraction pattern is generated using an X-ray diffractometer with a copper anode and a nickel filter.

2.15. Any foregoing form of Salt 2, in the form of a crystal having an X-ray powder diffraction pattern having at least 5, or at least 6, or at least 7, or at least 8, peaks having angle (2-theta) values and/or d-spacing values as provided in 2.13 and 2.14.

2.16. Any foregoing form of Salt 2, in the form of a crystal having an X-ray powder diffraction powder having relative angle (2-theta) values as provided in the table of embodiment 2.11, wherein the values are shifted by up to +/−0.2 degrees, e.g., wherein the values are substantially uniformly shifted by up to +/−0.2 degrees.

2.17. Any foregoing form of Salt 2 wherein the ITI-007 is deuterated, e.g., wherein the deuterium:protium ratio at one or more specified positions in the molecule is significantly higher, e.g., at least 2×, for example at least 10× higher, than the natural isotope ratios or the isotope ratios at other positions in the molecule at; for example, any foregoing form of Salt 2 wherein the —CH2- adjacent to the methylated nitrogen moiety and/or adjacent to the carbonyl moiety of ITI-007 is deuterated, e.g., is in the form of —CHD- or —CD2- at levels which are significantly higher than the natural deuterium:protium isotope ratio or the deuterium:protium isotope ratio at other positions in the molecule, and/or wherein the methyl group is deuterated, e.g., is CD3-, e.g., at levels which are significantly higher than the natural deuterium:protium isotope ratio or the deuterium:protium isotope ratio at other positions in the molecule, e.g., as described in WO 2015/154025, the contents of which are incorporated herein by reference.

2.18. Any foregoing form of Salt 2 exhibiting any combination of characteristics as described in 2.1-2.17.

In another embodiment, the invention provides a process for the production of Salt 2 (Process 2), comprising
(a) reacting 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with 4-aminosalicylic acid, e.g., together with an organic solvent, e.g., comprising methanol; e.g., wherein the 4-aminosalicylic acid and ITI-007 are in a molar ratio of about 1:1, and the solvent is methanol;
(b) optionally adding an anti-solvent, e.g., dibutyl ether;
(b) recovering the 4-aminosalicylate salt thus formed, e.g., recovering a 4-aminosalicylate salt according to any of Salt 2, et seq. above.

In another embodiment, the invention provides a method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising reacting a crude solution of ITI-007 with 4-aminosalicylic acid, and recovering the 4-aminosalicylate salt thus formed, e.g., in accordance with Process 2, and optionally converting the 4-aminosalicylate salt back to ITI-007 free base or to another salt form.

In another embodiment, the invention provides the use of 4-aminosalicylic acid in a method of isolating and/or purifying ITI-007.

In another embodiment, the invention provides a pharmaceutical composition comprising Salt 2, e.g., any of Salt 2.1-2.18, as active ingredient, in combination or association with a pharmaceutically acceptable diluent or carrier.

In another embodiment, the invention provides pharmaceutical composition comprising Salt 2, e.g., any of Salt 2.1-2.18, as active ingredient, in combination or association with a pharmaceutically acceptable diluent or carrier, wherein the Salt 2 is predominantly, or is entirely or substantially entirely, in dry crystalline form.

In a particular embodiment, the invention provides a pharmaceutical composition comprising Salt 2, e.g., any of Salt 2.1-2.18, as active ingredient, in combination or association with a pharmaceutically acceptable diluent or carrier, in the form of an injectable depot form, to provide extended release of ITI-007.

In another embodiment, the invention provides Salt 2, e.g., any of Salt 2.1-2.18, or a pharmaceutical composition comprising Salt 2, e.g., any of Salt 2.1-2.18, for use in treating a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia.

In another embodiment, the invention provides a method for the prophylaxis or treatment of a human suffering from a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulemia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia, comprising administering to a patient in need thereof a therapeutically effective amount of any of Salt 2, et seq.

Cyclamate Salts

In a first embodiment, the invention provides 1-(4-fluorophenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in cyclamate salt form (Salt 3). The invention therefore provides the following:

3.1. Salt 3 in solid form.
3.2. Salt 3 or 2.1 in dry crystalline form.
3.3. Salt 3.2 in a homogeneous crystal form, free or substantially free of other forms, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. % of amorphous forms.
3.4. Any foregoing form of Salt 3 in crystalline form, when crystallized from a mixture of cyclamic acid, e.g. in an organic solvent, e.g., comprising acetonitrile; e.g., wherein the cyclamic acid and ITI-007 are in a molar ratio of about 1:1, and the solvent is acetonitrile.
3.5. Any foregoing form of Salt 3 which is a solvate, e.g., an acetonitrile solvate.
3.6. Any foregoing form of Salt 3 which is not a solvate.
3.7. Any foregoing form of Salt 3 which is a hydrate.
3.8. Any foregoing form of Salt 3 which is not a hydrate.
3.9. Any foregoing form of Salt 3 formed by combining free ITI-007 free base and cyclamic acid in a 1:1 molar ratio.
3.10. Any foregoing form of Salt 3 wherein a DSC analysis shows three endothermic events, at 192° C., 245° C. and 301° C.; e.g. wherein a DSC/TGA analysis shows the first endothermic event at T$_{onset}$=180.4° C., T$_{peak}$=192.2° C. and ΔE=−109.8 J/g, the second at T$_{onset}$=236.8° C., T$_{peak}$=244.7° C. and ΔE=−143.6 J/g and the third at T$_{onset}$=268.1° C., T$_{peak}$=301.4° C. and ΔE=−954.61 J/g.
3.11. Any foregoing form of Salt 3, in the form of a crystal having an X-ray powder diffraction pattern corresponding to the d-spacing and/or angle (2-theta) values from the following table, for example at least five, or at least six, or at least seven, or at least eight of said values, e.g., taking into account potential variations due to sample purity and instrument variation, for example 2θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.2, e.g., at least 0.5, e.g., at least 0.6, e.g., comprising peaks 2, 7, 10 and 11:

| XRPD (Cu anode, Ni filter) for Cyclamate Salt Crystal | | | |
|---|---|---|---|
| # | Angle | d Value | Rel. Intensity |
| 1 | 6.448887 | 13.69484 | 0.005527 |
| 2 | 7.110893 | 12.4213 | 1 |
| 3 | 8.920965 | 9.904656 | 0.010137 |
| 4 | 11.62962 | 7.603136 | 0.010398 |
| 5 | 14.2128 | 6.226543 | 0.043874 |
| 6 | 14.97782 | 5.910188 | 0.041448 |
| 7 | 17.3469 | 5.107996 | 0.240146 |
| 8 | 18.45259 | 4.804338 | 0.020014 |
| 9 | 19.4362 | 4.563368 | 0.137812 |
| 10 | 19.94731 | 4.44758 | 0.200306 |
| 11 | 21.41874 | 4.145246 | 0.682959 |
| 12 | 21.81483 | 4.070868 | 0.089418 |
| 13 | 23.4386 | 3.792392 | 0.018596 |
| 14 | 24.71322 | 3.599606 | 0.014938 |
| 15 | 25.79342 | 3.451256 | 0.022498 |
| 16 | 27.43949 | 3.247841 | 0.040507 |
| 17 | 27.75534 | 3.211594 | 0.060059 |
| 18 | 28.68924 | 3.109137 | 0.010918 |
| 19 | 30.12954 | 2.963709 | 0.029668 |
| 20 | 30.86833 | 2.89444 | 0.039951 |
| 21 | 31.34743 | 2.851286 | 0.015544 |
| 22 | 31.84091 | 2.808213 | 0.003652 |
| 23 | 33.46514 | 2.675536 | 0.007115 |
| 24 | 33.87624 | 2.644001 | 0.029155 |
| 25 | 35.09081 | 2.555218 | 0.005425 |
| 26 | 36.09988 | 2.486075 | 0.070898 |
| 27 | 37.12529 | 2.41973 | 0.02435 |
| 28 | 37.33543 | 2.406592 | 0.031208 |
| 29 | 38.75318 | 2.321749 | 0.004214 |
| 30 | 39.55663 | 2.276423 | 0.005349 |
| 31 | 41.01483 | 2.198793 | 0.025186 |
| 32 | 42.02842 | 2.148079 | 0.003309 |
| 33 | 43.22437 | 2.091375 | 0.016996 |
| 34 | 43.68925 | 2.070193 | 0.003216 |
| 35 | 44.56517 | 2.031516 | 0.010776 |

3.12. Any foregoing form of Salt 3, in the form of a crystal having an X-ray powder diffraction pattern corresponding to FIG. 3, e.g., taking into account potential variations due to sample purity and instrument variation, for example 2θ shifts due to variation in X-ray wavelength, e.g., an X-ray powder diffraction pattern corresponding to FIG. 3 generated using an X-ray diffractometer with a copper anode and a nickel filter.
3.13. Any foregoing form of Salt 3, in the form of a crystal having an X-ray powder diffraction pattern having at least 5, or at least 6, or at least 7, or at least 8, peaks having angle (2-theta) values selected from the group consisting of about 6.45, 7.11, 8.92, 11.63, 14.21, 14.98, 17.35, 18.45, 19.44, 19.95, 21.42, 21.81, 23.44, 24.71, 25.79, 27.44, 27.76, 28.69, 30.13, 30.87, 31.35, 31.84, 33.47, 33.88, 35.09, 36.10, 37.13, 37.34, 38.75, 39.56, 41.02, 42.03, 43.33, 43.69, and 44.57, taking into account potential variations due to sample purity and instrument variation, wherein the X-ray powder diffraction pattern is generated using an X-ray diffractometer with a copper anode and a nickel filter.
3.14. Any foregoing form of Salt 3, in the form of a crystal having an X-ray powder diffraction pattern having at least 5, or at least 6, or at least 7, or at least 8, peaks having d-spacing values selected from the group consisting of about 13.69, 12.42, 9.90, 7.60, 6.23, 5.91, 5.11, 4.80, 4.56, 4.45, 4.15, 4.07, 3.79, 3.60, 3.45, 3.25, 3.21, 3.11, 2.96, 2.89, 2.85, 2.81, 2.68, 2.64, 2.56, 2.49, 2.42, 2.41, 2.32, 2.28, 2.20, 2.15, 2.09, 2.07, and 2.03, taking into account potential variations due to sample purity and instrument variation, wherein the X-ray powder diffraction pattern is generated using an X-ray diffractometer with a copper anode and a nickel filter.

3.15. Any foregoing form of Salt 3, in the form of a crystal having an X-ray powder diffraction pattern having at least 5, or at least 6, or at least 7, or at least 8, peaks having angle (2-theta) values and/or d-spacing values as provided in 3.13 and 3.14.

3.16. Any foregoing form of Salt 3, in the form of a crystal having an X-ray powder diffraction powder having relative angle (2-theta) values as provided in the table of embodiment 3.11, wherein the values are shifted by up to +/−0.2 degrees, e.g., wherein the values are substantially uniformly shifted by up to +/−0.2 degrees.

3.17. Any foregoing form of Salt 3 wherein the ITI-007 is deuterated, e.g., wherein the deuterium:protium ratio at one or more specified positions in the molecule is significantly higher, e.g., at least 2×, for example at least 10× higher, than the natural isotope ratios or the isotope ratios at other positions in the molecule at; for example, any foregoing form of Salt 3 wherein the —CH2- adjacent to the methylated nitrogen moiety and/or adjacent to the carbonyl moiety of ITI-007 is deuterated, e.g., is in the form of —CHD- or —CD2- at levels which are significantly higher than the natural deuterium:protium isotope ratio or the deuterium:protium isotope ratio at other positions in the molecule, and/or wherein the methyl group is deuterated, e.g., is CD3-, e.g., at levels which are significantly higher than the natural deuterium:protium isotope ratio or the deuterium:protium isotope ratio at other positions in the molecule, e.g., as described in WO 2015/154025, the contents of which are incorporated herein by reference.

3.18. Any foregoing form of Salt 3 exhibiting any combination of characteristics as described in 2.1-2.17.

In another embodiment, the invention provides a process for the production of Salt 3, comprising
(a) reacting 1-(4-fluoro-phenyl)-4-((6bR,10aS)-3-methyl-2,3,6b,9,10,10a-hexahydro-1H,7H-pyrido[3',4':4,5] pyrrolo[1,2,3-de]quinoxalin-8-yl)-butan-1-one (ITI-007) free base with cyclamic acid, e.g., together with an organic solvent, e.g., comprising acetonitrile; e.g., wherein the cyclamic acid and ITI-007 are in a molar ratio of about 1:1, and the solvent is acetonitrile; and
(b) recovering the cyclamate salt thus formed, e.g., recovering a cyclamate salt according to any of Salt 3, et seq. above.

In another embodiment, the invention provides a method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising reacting a crude solution of ITI-007 with 4-aminosalicylic acid, and recovering the 4-aminosalicylate salt thus formed, e.g., in accordance with Process 2, and optionally converting the 4-aminosalicylate salt back to ITI-007 free base or to another salt form.

In another embodiment, the invention provides the use of 4-aminosalicylic acid in a method of isolating and/or purifying ITI-007.

In another embodiment, the invention provides a pharmaceutical composition comprising Salt 3, e.g., any of Salt 3.1-3.18, as active ingredient, in combination or association with a pharmaceutically acceptable diluent or carrier.

In another embodiment, the invention provides a pharmaceutical composition comprising Salt 3, e.g., any of Salt 3.1-3.18, as active ingredient, in combination or association with a pharmaceutically acceptable diluent or carrier, wherein the Salt 3 is predominantly, or is entirely or substantially entirely, in dry crystalline form.

In a particular embodiment, the invention provides a pharmaceutical composition comprising Salt 3, e.g., any of Salt 3.1-3.18, as active ingredient, in combination or association with a pharmaceutically acceptable diluent or carrier, in the form of an injectable depot form, to provide extended release of ITI-007.

In another embodiment, the invention provides Salt 3, e.g., any of Salt 3.1-3.18, or a pharmaceutical composition comprising Salt 3, e.g., any of Salt 3.1-3.18, for use in treating a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia.

In another embodiment, the invention provides a method for the prophylaxis or treatment of a human suffering from a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia, comprising administering to a patient in need thereof a therapeutically effective amount of any of Salt 3, et seq.

EXAMPLES

The following equipment and methods are used to isolate and characterize the exemplified salt forms:

X-Ray Powder Diffraction (XRPD):

The X-ray powder diffraction studies are performed using a Bruker AXS D2 PHASER in Bragg-Brentano configuration, equipment #1549/#2353. The equipment uses a Cu anode at 30 kV, 10 mA; sample stage standard rotating; monochromatization by a Kβ-filter (0.5% Ni). Slits: fixed divergence slits 1.0 mm (=0.61°), primary axial Soller slit 2.5°, secondary axial Soller slit 2.5°. Detector: Linear detector LYNXEYE with receiving slit 5° detector opening. The standard sample holder (0.1 mm cavity in (510) silicon wafer) has a minimal contribution to the background signal. Measurement conditions: scan range 5-45° 2θ, sample rotation 5 rpm, 0.5 s/step, 0.010°/step, 3.0 mm detector slit; and all measuring conditions are logged in the instrument control file. As system suitability, corundum sample A26-B26-S (NIST standard) is measured daily. The software used for data collection is Diffrac.Commander v2.0.26. Data analysis is done using Diffrac.Eva v1.4. No background correction or smoothing is applied to the patterns.

Simultaneous Thermogravimetry (TGA) and Differential Scanning Calorimetry (DSC) or TGA/DSC Analysis:

The TGA/DSC studies are performed using a Mettler Toledo TGA/DSC1 Stare System, equipment #1547, autosampler equipped, using pin-holed Al-crucibles of 40 μl. Measurement conditions: 5 min 30.0° C., 30.0-350.0° C.

with 10° C./min., N2 flow of 40 ml/min. The software used for instrument control and data analysis is STARe v12.10.

Differential Scanning Calorimetry (DSC):

The DSC studies are performed using a Mettler Toledo DSC1 STARe System, equipment #1564. The samples are made using Al crucibles (40 µl; pierced). Typically 1-8 mg of sample is loaded onto a pre-weighed Al crucible and is kept at 30° C. for 5 minutes, after which it is heated at 10° C./min from 30° C. to 350° C. and kept at 350° C. for 1 minute. A nitrogen purge of 40 ml/min is maintained over the sample. As system suitability check Indium and Zinc are used as references. The software used for data collection and evaluation is STARe Software v12.10 build 5937. No corrections are applied to the thermogram.

Polarized Light Microscopy (PLM):

The microscopy studies are performed using an AxioVert 35M, equipped with an AxioCamERc 5s, equipment #1612. The microscope is equipped with four lenses: Zeiss A-Plan 5×/0.12, Zeiss A-Plan 10×/0.25, LD A-Plan 20×/0.30 and Achros TIGMAT 32×/0.40. Data collection and evaluation is performed using Carl Zeiss Zen AxioVision Blue Edition Lite 2011 v1.0.0.0 software. A small amount of sample is loaded on an object glass and carefully spread until a thin layer is obtained.

Dynamic Vapour Sorption (DVS):

The Dynamic Vapour Sorption studies are performed using a Surface Measurement Systems Ltd. DVS-1 No Video, equipment #2126. The sample is loaded into a balance pan, typically 20-30 mg, and equilibrated at 0% RH. After the material was dried, the RH is increased with 10% per step for 1 hour per increment, ending at 95% RH. After completion of the sorption cycle, the sample was dried using the same method. The software used for data collection is DVSWin v3.01 No Video. Data analysis is performed using DVS Standard Analysis Suite v6.3.0 (Standard).

Particle Size Distribution (PSD):

The particle size distribution studies are performed using a Malvern Instruments Mastersizer, equipment #1712. The Mastersizer uses a 300RF lens range of 0.05 µm-900 mm. Polydisperse is used as analysis model. Measurement conditions: before each sample measurement a background measurement is performed, the background scan time is 12 seconds (12000 snaps). Each sample is dispersed in Multipar G, refractive index of 1.42. The obscuration range on sample dispersion is between 10%-30%. Each sample is measured 6 times at t=0 and t=30 minutes and the measurement scan time is 10 seconds (10000 snaps). The targeted stirring speed of the sample dispersion unit is 2000±10 rpm. Data collection and evaluation is performed using Mastersizer S Version 2.19 software.

Capillary Melting Point:

The capillary melting point is determined on a Büchi Melting Point B-545, equipment #000011, conform USP guidelines.

X-Ray Fluorescence (XRF):

The X-ray fluorescence studies are performed using a Bruker AXS S2 RANGER, equipment #2006. Using an end-window X-ray tube with Palladium anode and an ultrathin Beryllium window (75 µm) for superior light element analysis. As detector the Xflash V5 detector with Cr, Ti, Al, Ta collimator (energy resolution <129 eV FWHM at 100 000 cps Mnkα) is used. The S2 Ranger is equipped with an autosampler with integrated 28 position X-Y automatic sample changer with exchangeable tray, which allows maximum sample diameter of 40 mm. Samples are mounted in steel rings of 51.5 mm diameter for automatic operation. Measurement conditions: disposable liquid cups (35 mm inner diameter, 40 mm outer diameter) with polypropylene foil 5 µm. As system suitability check a copper disk is measured daily and a glass disk, containing several elements, is measured weekly. The software used for data collection is S2 Ranger Control Software V4.1.0. Data analysis is performed using SPECTRA EDX V2.4.3 evaluation software. No background correction or smoothing is applied to the patterns.

Fourier Transform Infrared Spectroscopy (FT-IR):

The FT-IR studies are performed using a Thermo Scientific Nicolet iS50, equipment #2357. An attenuated total reflectance (ATR) technique was used with a beam splitter of KBr. Experiment setup of the collected sample is used number of scans 16 with a resolution of 4 from 400 $cm^{-1}$ to 4000 $cm^{-1}$. The software OMNIC version 9.2 is used for data collection and evaluation.

Thermogravimetric Analysis (TGA) with Infrared Spectroscopy (TGA-IR):

In TGA-IR, the off-gassing materials are directed through a transfer line to a gas cell, where the infrared light interacts with the gases. The temperature ramp and first derivative weight loss information from the TGA is shown as a Gram-Schmidt (GS) profile; the GS profile essentially shows the total change in the IR signal relative to the initial state. In most cases, the GS and the derivative weight loss will be similar in shape, although the intensity of the two can differ. For this experiment are two devices coupled to each other. The TGA studies are performed using a Mettler Toledo TGA/DSC1 STARe System with a 34-position auto sampler, equipment #1547. The samples are made using Al crucibles (100 µl; pierced). Typically 20-50 mg of sample is loaded into a pre-weighed Al crucible and is kept at 30° C. for 5 minutes after which it is heated at 10° C./min from 30° C. to 350° C. A nitrogen purge of 40 ml/min is maintained over the sample. The TGA-IR module of the Nicolet iS50 is coupled to the TGA/DSC1. The IR studies were performed using a Thermo Scientific Nicolet iS50, equipment #2357. Experiment setup of the collected series, the profile Gram-Schmidt is used number of scans 10 with a resolution of 4. The software OMNIC version 9.2 is used for data collection and evaluation.

High Performance Liquid Chromatography (HPLC):

The high performance liquid chromatography analyses are performed on LC-31, equipped with an Agilent 1100 series G1322A degasser equipment #1894, an Agilent 1100 series G1311A quaternary pump equipment #1895, an Agilent 1100 series G1313A ALS equipment #1896, an Agilent 1100 series G1318A column equipment #1897 and an Agilent 1100 series G1314A VWD equipment #1898/LC-34, equipped with an Agilent 1200 series G1379B degasser equipment #2254, an Agilent 1100 series G1311A quaternary pump equipment #2255, Agilent 1100 series G1367A WPALS equipment #1656, an Agilent 1100 series G1316A column equipment #2257 and an Agilent 1100 series G1315B DAD equipment #2258. Data is collected and evaluated using Agilent ChemStation for LC systems Rev. B.04.02[96]. Solutions are prepared as follows: Mobile phase A: Add 800 ml of MilliQ water to a 1 L volumetric flask. Add 1 ml of TFA and homogenize. Fill up to the mark with MilliQ; Mobile phase B: Add 800 ml of Acetonitrile to a 1 L volumetric flask. Add 1 ml of TFA and homogenize. Fill up to the mark with Acetonitrile; Diluent: 50/50 MeOH/ACN.

Example 1: Oxalate Salt Crystal

Solubility of free base in various solvents is evaluated, and based on the results of the solubility range, suitable solvents are selected for the salt screen. The salt screen is divided into seven separate screens, using 90 different counter ions, six different solvents, and including four different crystallization methods, slurry experiments, cooling crystallization, evaporation and precipitation experiments. The counterions are selected based upon availability and potential suitability to form pharmaceutically acceptable acid addition salts. They include the class I, II and III acids identified in Stahl P. H., Wermuch C. G. (editors), Handbook of Pharmaceutical Salts, IUPAC (2008).

Figure 1:
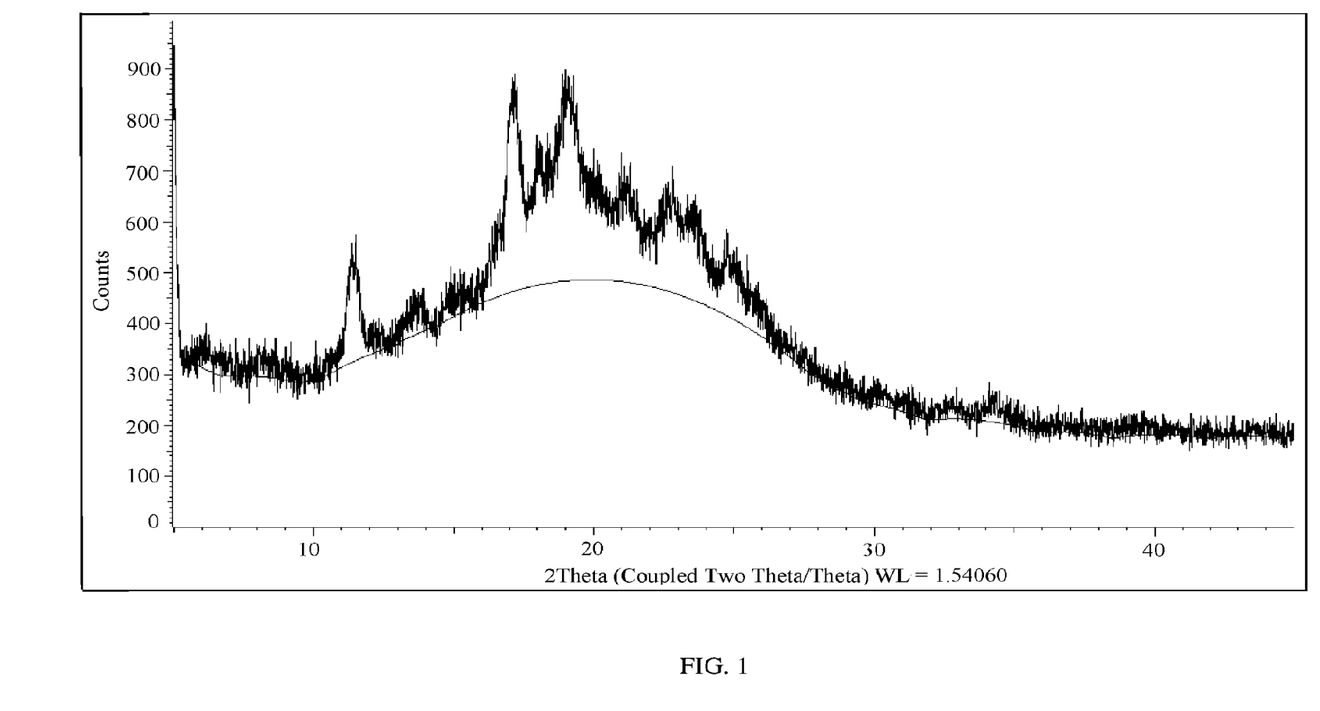
FIG. 1 depicts an X-ray powder diffraction pattern for an ITI-007 oxalate salt crystal.

An oxalate salt of ITI-007 is obtained in the course of salt screening from a slurry in ethyl acetate. FT-IR of the ITI-007 oxylate salt formed in the experiments using oxalic acid shows 80% similarity with the FT-IR of the free base and ~5-10% similarity with that of oxalic acid itself. In addition, LC analysis shows no decomposition of the free base moiety of the formed salt, meaning an oxalate salt of ITI-007 has formed. This experiment is then repeated at gram scale and a concentration of 100 mg/mL of ITI-007 free base is used. The free base and oxalic acid are added in a 1:1 ratio, and then ethyl acetate is added. The mixture is slurried at 50° C. for 2 hours. The mixture is allowed to cool down to room temperature and is filtered and dried to give a yellow (sticky) solid. XRPD analysis shows the oxalate to be a poor crystalline solid. The XRPD pattern is shown in FIG. 1; the peaks are identified in tabular form in table 1:

TABLE 1

XRPD peak list oxalate salt

| # | Angle | d Value | Rel. Intensity |
|---|---|---|---|
| 1 | 11.36753 | 7.77784 | 0.505801 |
| 2 | 11.4984 | 7.689606 | 0.535533 |
| 3 | 13.63323 | 6.489913 | 0.201991 |
| 4 | 14.90435 | 5.939156 | 0.242149 |
| 5 | 16.28162 | 5.439727 | 0.225224 |
| 6 | 17.06375 | 5.192113 | 1 |
| 7 | 17.08605 | 5.185387 | 0.95063 |
| 8 | 18.92882 | 4.684528 | 0.973955 |
| 9 | 18.98987 | 4.669604 | 0.896333 |
| 10 | 20.91385 | 4.244165 | 0.483429 |
| 11 | 22.84175 | 3.890119 | 0.493607 |
| 12 | 23.80149 | 3.735387 | 0.38255 |
| 13 | 24.77138 | 3.591286 | 0.36959 |

The oxalate salt is also analyzed by DSC/TGA, DVS, HPLC, $^1$H-NMR and FT-IR. DSC/TGA analysis shows two endothermic events, the first at $T_{onset}$=74.5° C., $T_{peak}$=83.3° C. and ΔE=−6.0 J/g and the second at $T_{onset}$=194.2° C., $T_{peak}$=218.6° C. and ΔE=−162.1.0 J/g. Both endothermic events are linked to a mass loss of 8.5% and 12.0% respectively, meaning a solvate has formed. Analysis of the HPLC data shows a purity of 91-area %. Analysis of the $^1$H-NMR data shows some shifts compared to the free base, which confirms the salt formation. FT-IR analysis confirms the chemical structure. DVS analysis shows some stepwise sorption; the total mass uptake at 95 RH % is 5%, so the oxalate salt is moderately hygroscopic.

TABLE 2

Analytical results scale-up synthesis of the oxalate salt

| Solvent | Appearance | DVS Hygroscopicity (%) | DSC ($T_{peak}$ ° C.) | DVS: Mass loss (%) | HPLC purity (area %) |
|---|---|---|---|---|---|
| Ethyl acetate | Yellow sticky solid | 5 | 83 219 | 8 12 | 91 |

Example 2: 4-Aminosalicylate Salt Crystal

Figure 2:
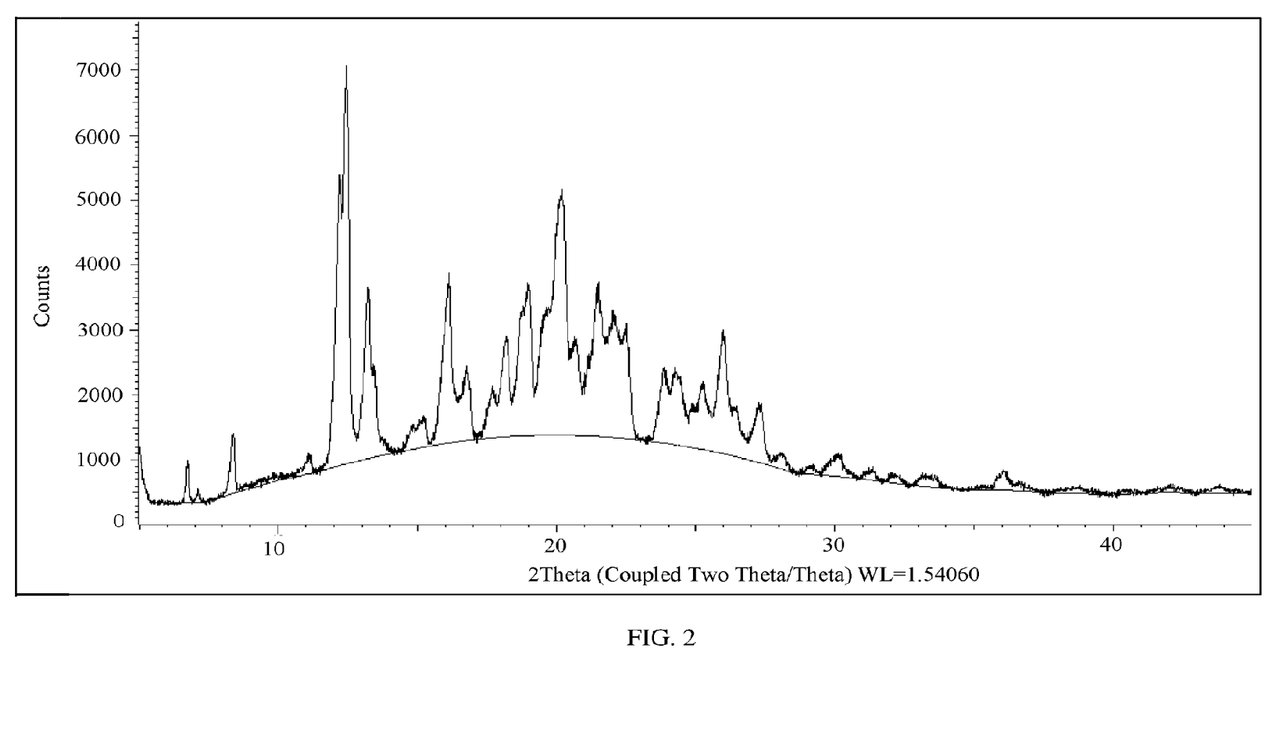
FIG. 2 depicts an X-ray powder diffraction pattern for an ITI-007 4-aminosalicylate salt crystal.

A 4-aminosalicylate salt is obtained in screening in a precipitation experiment using methanol. This experiment is repeated at a gram scale. The ITI-007 free base and 4-aminosalicylic acid (ratio 1:1) are dissolved in methanol (5 mL) and then dibutylether is added as an anti-solvent (10 mL). The mixture is shaken at room temperature and a yellow solid is precipitated. The yellow solid is filtered, dried and analyzed by XRPD. XRPD analysis shows the 4-aminosalicilate salt to be crystalline. The XRPD pattern is shown in FIG. 2; the peaks are identified in tabular form in table 3:

TABLE 3

XRPD peak list 4-aminosalicylate salt

| # | Angle | d Value | Rel. Intensity |
|---|---|---|---|
| 1 | 6.74126 | 13.10153 | 0.09900139 |
| 2 | 7.11907 | 12.40705 | 0.03797358 |
| 3 | 8.37464 | 10.54953 | 0.1528345 |
| 4 | 11.10135 | 7.963726 | 0.04906989 |
| 5 | 12.24933 | 7.219841 | 0.7057194 |
| 6 | 12.44248 | 7.108195 | 1 |
| 7 | 13.22133 | 6.691157 | 0.4287872 |
| 8 | 13.39928 | 6.602692 | 0.2176722 |
| 9 | 14.84852 | 5.96136 | 0.0594308 |
| 10 | 15.20714 | 5.821574 | 0.08040762 |
| 11 | 16.11707 | 5.494892 | 0.3971254 |
| 12 | 16.77107 | 5.28206 | 0.1820023 |
| 13 | 17.7106 | 5.003911 | 0.1346539 |
| 14 | 17.7024 | 5.006211 | 0.117254 |
| 15 | 18.18279 | 4.875015 | 0.2468108 |
| 16 | 18.8011 | 4.716061 | 0.3306873 |
| 17 | 18.97436 | 4.673387 | 0.3899686 |
| 18 | 19.70455 | 4.501822 | 0.3229629 |
| 19 | 20.18032 | 4.396748 | 0.6070609 |
| 20 | 20.6671 | 4.294276 | 0.2430615 |
| 21 | 21.48864 | 4.131919 | 0.3574843 |
| 22 | 22.0719 | 4.024034 | 0.307444 |
| 23 | 22.47136 | 3.953394 | 0.270866 |
| 24 | 23.8674 | 3.72522 | 0.1904099 |
| 25 | 24.28923 | 3.661472 | 0.1862242 |
| 26 | 24.39947 | 3.645177 | 0.1742721 |
| 27 | 24.93711 | 3.567793 | 0.09287543 |
| 28 | 25.24371 | 3.52515 | 0.1587876 |
| 29 | 25.98695 | 3.425991 | 0.3154892 |
| 30 | 26.41592 | 3.37132 | 0.1229696 |
| 31 | 27.28763 | 3.26557 | 0.1484904 |
| 32 | 27.30054 | 3.264055 | 0.1485404 |
| 33 | 28.05261 | 3.178234 | 0.03697395 |
| 34 | 30.12185 | 2.964448 | 0.0494277 |
| 35 | 33.52555 | 2.670852 | 0.02418169 |
| 36 | 35.96252 | 2.495255 | 0.0386623 |
| 37 | 36.2068 | 2.478979 | 0.03238863 |
| 38 | 36.07337 | 2.487841 | 0.04954784 |

The 4-aminosalicylate salt is also analyzed by DVS, DSC/TGA and HPLC, the results are summarized in table 4. DSC/TGA analysis shows two endothermic events, the first at $T_{onset}$=119.1° C., $T_{peak}$=125.4° C. and ΔE=−26.8 J/g and the second at $T_{onset}$=142.3° C., $T_{peak}$=166.3° C. and ΔE=−

115.9 J/g. TGA shows three different mass losses, 1.8% in the temperature range of 40° C.-120° C., 10.8% in the temperature range 120° C.-190° C. and 13.8% in the temperature range of 190-260° C. The material decomposes above 260° C. Analysis of the HPLC data shows a purity of 78-area %. Analysis of the $^1$H-NMR data shows shift compared to the free base, both the free base and 4-aminosalicylic acid are present, which confirms the salt formation. FT-IR analysis confirms the chemical structure. Analysis of the DVS data shows a stepwise sorption with a total mass uptake of 5% (at 95 RH %), which indicates the 4-aminosalicylate is moderately hygroscopic.

TABLE 4

Analytical results scale-up synthesis of the 4-aminosalicylate salt

| Solvent | Appearance | DVS Hygroscopicity (%) | DSC ($T_{peak}$ ° C.) | Mass loss (%) | HPLC purity (area %) |
|---|---|---|---|---|---|
| Methanol | Yellow solid | 5 | 125<br>166 | 2<br>11<br>14 | 78 |

Example 3: Cyclamate Salt Crystal

Figure 3:
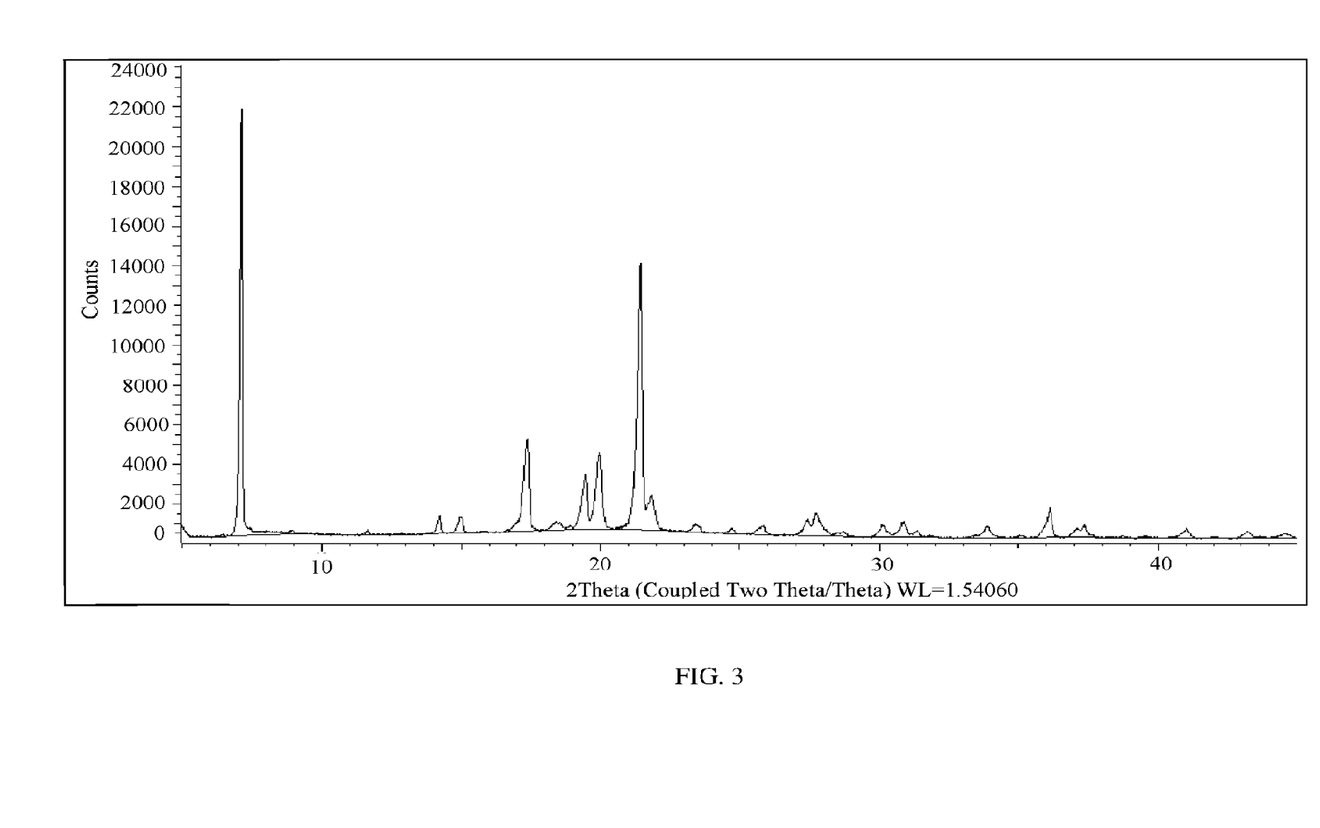
FIG. 3 depicts an X-ray powder diffraction pattern for an ITI-007 cyclamate salt crystal.

A cyclamate salt of ITI-007 is obtained by screening in a slurry experiment in acetonitrile. This experiment is repeated at gram scale using a concentration of 100 mg/mL ITI-007 free base. The free base and cyclamic acid are added in 1:1 ratio, and then acetonitrile is added and the mixture is slurried at 50° C. for 2 hours. The mixture is allowed to cool down to room temperature, then filtered and dried to give an off white powder. XRPD analysis shows the cyclamate to be a crystalline powder. The XRPD pattern is shown in FIG. 3; the peaks are identified in tabular form in table 5:

TABLE 5

XRPD peak list of the cyclamate salt

| # | Angle | d Value | Rel. Intensity |
|---|---|---|---|
| 1 | 6.448887 | 13.69484 | 0.005527 |
| 2 | 7.110893 | 12.4213 | 1 |
| 3 | 8.920965 | 9.904656 | 0.010137 |
| 4 | 11.62962 | 7.603136 | 0.010398 |
| 5 | 14.2128 | 6.226543 | 0.043874 |
| 6 | 14.97782 | 5.910188 | 0.041448 |
| 7 | 17.3469 | 5.107996 | 0.240146 |
| 8 | 18.45259 | 4.804338 | 0.020014 |
| 9 | 19.4362 | 4.563368 | 0.137812 |
| 10 | 19.94731 | 4.44758 | 0.200306 |
| 11 | 21.41874 | 4.145246 | 0.682959 |
| 12 | 21.81483 | 4.070868 | 0.089418 |
| 13 | 23.4386 | 3.792392 | 0.018596 |
| 14 | 24.71322 | 3.599606 | 0.014938 |
| 15 | 25.79342 | 3.451256 | 0.022498 |
| 16 | 27.43949 | 3.247841 | 0.040507 |
| 17 | 27.75534 | 3.211594 | 0.060059 |
| 18 | 28.68924 | 3.109137 | 0.010918 |
| 19 | 30.12954 | 2.963709 | 0.029668 |
| 20 | 30.86833 | 2.89444 | 0.039951 |
| 21 | 31.34743 | 2.851286 | 0.015544 |
| 22 | 31.84091 | 2.808213 | 0.003652 |
| 23 | 33.46514 | 2.675536 | 0.007115 |
| 24 | 33.87624 | 2.644001 | 0.029155 |
| 25 | 35.09081 | 2.555218 | 0.005425 |
| 26 | 36.09988 | 2.486075 | 0.070898 |
| 27 | 37.12529 | 2.41973 | 0.02435 |
| 28 | 37.33543 | 2.406592 | 0.031208 |

TABLE 5-continued

XRPD peak list of the cyclamate salt

| # | Angle | d Value | Rel. Intensity |
|---|---|---|---|
| 29 | 38.75318 | 2.321749 | 0.004214 |
| 30 | 39.55663 | 2.276423 | 0.005349 |
| 31 | 41.01483 | 2.198793 | 0.025186 |
| 32 | 42.02842 | 2.148079 | 0.003309 |
| 33 | 43.22437 | 2.091375 | 0.016996 |
| 34 | 43.68925 | 2.070193 | 0.003216 |
| 35 | 44.56517 | 2.031516 | 0.010776 |

The cyclamate salt of ITI-007 is also analyzed by DVS, DSC/TGA and HPLC. The results are summarized in table 20. DSC/TGA analysis shows three endothermic events, the first at $T_{onset}$=180.4° C., $T_{peak}$=192.2° C. and $\Delta E$=−109.8 J/g, the second at $T_{onset}$=236.8° C., $T_{peak}$=244.7° C. and $\Delta E$=−143.6 J/g and the third at $T_{onset}$=268.1° C., $T_{peak}$=301.4° C. and $\Delta E$=−954.61 J/g. The third endothermic event represents decomposition of the compound, confirmed by the corresponding mass loss of 56.3%. TGA shows another mass loss of 19.9% in the temperature range of 180° C.-260° C. Analysis of the HPLC data shows a purity of 67 area %. Analysis of the $^1$H-NMR data show some shifts compared to the free base, both the free base and cyclamic acid are present, which confirms the cyclamate salt formation. FT-IR analysis confirms the chemical structure. Analysis of the DVS data shows stepwise sorption with at total mass uptake of 8% at 95 RH %, meaning the cyclamate salt is somewhat hygroscopic.

TABLE 6

Analytical results scale-up synthesis of the FP-212 cyclamate salt.

| Solvent | Appearance | DVS Hygroscopicity (%) | DSC ($T_{peak}$ ° C.) | Mass loss (%) | HPLC purity (area %) |
|---|---|---|---|---|---|
| Acetonitrile | White powder | 8 | 192<br>245<br>301 | 20<br>56 | 67 |

The invention claimed is:

1. A salt of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007), wherein the salt is selected from the oxalate, the 4-aminosalicylate, and the cyclamate, and wherein the salt is in crystalline form.

2. The salt according to claim 1 which is an oxalate salt crystal having an X-ray diffraction pattern substantially corresponding to FIG. 1.

3. The salt according to claim 1 which is a 4-aminosalicylate salt crystal having an X-ray diffraction pattern substantially corresponding to FIG. 2.

4. The salt according to claim 1 which is a cyclamate salt crystal having an X-ray diffraction pattern substantially corresponding to FIG. 3.

5. A method making a salt according to claim 1, comprising (a) reacting 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with an acid selected from oxalic acid, 4-aminosalicylic acid, and cyclamic acid, and (b) recovering the salt thus formed.

6. A method of purifying 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in free or salt form, comprising reacting crude ITI-007 with an acid selected from oxalic acid, 4-aminosalicylic acid, and cyclamic acid, recovering the salt thus formed, wherein the salt is in crystalline form, and optionally converting the oxalate salt or 4-aminosalicylate salt or cyclamate salt back to ITI-007 free base or to another salt form.

7. A method for the prophylaxis or treatment of a human suffering from a disease or abnormal condition involving or mediated by the 5-HT2A receptor, serotonin transporter (SERT), and/or dopamine $D_1/D_2$ receptor signaling pathways comprising administering to said human an effective amount of a salt according to claim 1, wherein the disease or abnormal condition is selected from obesity, anorexia, bulimia, depression, anxiety, psychosis, schizophrenia, migraine, obsessive-compulsive disorder, sexual disorders, attention deficit disorder, attention deficit hyperactivity disorder, sleep disorders, conditions associated with cephalic pain, social phobias, and dementia.

8. A pharmaceutical composition comprising a salt according to claim 1, in combination or association with a pharmaceutically acceptable diluent or carrier.

9. The salt according to claim 1, wherein the salt is in a homogeneous crystal form, free or substantially free of other forms.

10. The salt according to claim 9, wherein the salt is in a homogeneous crystal form, free or substantially free of any amorphous forms of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one.

11. The salt according to claim 10, wherein the co crystal salt comprises less than 2 wt. % of any amorphous forms of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one.

12. The salt according to claim 1 which is an oxalate salt.

13. The salt according to claim 1 which is a 4-aminosalicylate salt.

14. The salt according to claim 1 which is a cyclamate salt.

15. The method according to claim 6, wherein the oxalate salt or 4-aminosalicylate salt or cyclamate salt is converted back to ITI-007 free base.

16. The method according to claim 6, wherein the oxalate salt or 4-aminosalicylate salt or cyclamate salt is converted to ITI-007 in tosylate salt form.

17. The method according to claim 7, wherein the disease or abnormal condition is selected from depression, anxiety, psychosis, schizophrenia, obsessive-compulsive disorder, attention deficit disorder, attention deficit hyperactivity disorder, sleep disorders, social phobias, and dementia.

18. The method according to claim 17, wherein the disease or abnormal condition is selected from depression, anxiety, psychosis, schizophrenia, and dementia.

* * * * *